(12) United States Patent
Jagiella et al.

(10) Patent No.: US 7,023,564 B2
(45) Date of Patent: Apr. 4, 2006

(54) SENSOR DEVICE FOR BURR EXAMINATION

(75) Inventors: Manfred Jagiella, Notzingen (DE); Sorin Fericean, Leonberg (DE)

(73) Assignee: Balluff GmbH, Neuhausen (DE)

(*) Notice: Subject to any disclaimer, the term of this patent is extended or adjusted under 35 U.S.C. 154(b) by 299 days.

(21) Appl. No.: 10/047,447

(22) Filed: Jan. 14, 2002

(65) Prior Publication Data

US 2002/0135361 A1   Sep. 26, 2002

(30) Foreign Application Priority Data

Jan. 22, 2001   (DE) ............................. 101 03 177

(51) Int. Cl.
*G01B 11/14*   (2006.01)

(52) U.S. Cl. ................. 356/614; 356/237.1; 356/241.1

(58) Field of Classification Search .. 356/237.1–237.6, 356/614–623, 241.1, 241.2, 241.3, 241.4, 356/241.5; 324/207.17; 451/5, 6; 901/9, 901/41; 318/568.22
See application file for complete search history.

(56) References Cited

U.S. PATENT DOCUMENTS

| | | | |
|---|---|---|---|
| 3,327,584 A | | 6/1967 | Kissinger |
| 4,199,258 A | | 4/1980 | Dau |
| 4,465,374 A | | 8/1984 | Pryor et al. |
| 4,567,347 A | * | 1/1986 | Ito et al. ............... 219/124.34 |
| 4,777,769 A | * | 10/1988 | McLaughlin et al. ......... 451/5 |
| 4,824,248 A | * | 4/1989 | Neumann ................... 356/244 |
| 4,894,597 A | * | 1/1990 | Ohtomi ................ 318/568.22 |
| 4,942,672 A | | 7/1990 | Yoshida |
| 4,967,092 A | | 10/1990 | Fraignier et al. |
| 5,119,030 A | * | 6/1992 | Bossard et al. ............. 324/456 |
| 5,243,265 A | * | 9/1993 | Matsuura et al. ........... 318/578 |
| 5,302,894 A | | 4/1994 | Hrubes |
| 5,473,156 A | | 12/1995 | Pinnock et al. |
| 5,485,082 A | | 1/1996 | Wisspeintner et al. |
| 5,523,685 A | * | 6/1996 | Kasai et al. ................. 324/229 |
| 5,942,693 A | | 8/1999 | Harms et al. |
| 5,988,971 A | * | 11/1999 | Fossey et al. .......... 414/416.01 |

(Continued)

FOREIGN PATENT DOCUMENTS

DE   38 39 386   5/1990

(Continued)

OTHER PUBLICATIONS

Patent Abstracts of Japan, Abstract of Japanese Patent "Burr Removing Robot Control Method", Publication No. 04310360, Nov. 2, 1992, Japanese Application No. 03072794, Filed Apr. 5, 1991.

(Continued)

*Primary Examiner*—Hoa Q. Pham
(74) *Attorney, Agent, or Firm*—Lipsitz & McAllister, LLC (57) ABSTRACT

In order to provide a burr examination sensor device for the examination of burrs on a workpiece which can be used universally it is suggested that this comprise at least one distance sensor with a detector head, wherein the detector head can be positioned at a distance to the workpiece and detector head and workpiece are movable relative to one another and wherein the detector head can be coupled electromagnetically to the workpiece or the workpiece can be acted upon by it with an electromagnetic signal and the coupling to the workpiece or an electromagnetic reaction signal of the workpiece to the impinging signal are dependent on a distance between detector head and workpiece so that this distance can be determined without any contact and a workpiece surface can be scanned by the detector head without any contact.

44 Claims, 6 Drawing Sheets

U.S. PATENT DOCUMENTS

| | | | | |
|---|---|---|---|---|
| 6,155,757 | A | * | 12/2000 | Neumann .................... 409/131 |
| 6,628,408 | B1 | * | 9/2003 | Franklin et al. ............ 356/623 |
| 2004/0136010 | A1 | | 7/2004 | Jensen et al. |
| 2005/0172726 | A1 | * | 8/2005 | Jagiella et al. ................. 73/779 |

FOREIGN PATENT DOCUMENTS

| | | |
|---|---|---|
| DE | 39 10 297 | 10/1990 |
| DE | 40 40 084 | 6/1992 |
| DE | 41 02 721 | 8/1992 |
| DE | 42 17 292 | 12/1993 |
| DE | 42 31 989 | 1/1994 |
| DE | 42 32 827 | 3/1994 |
| DE | 196 24 233 | 10/1997 |
| DE | 198 47 365 | 5/2000 |
| DE | 198 53 302 | 5/2000 |
| EP | 0 557 558 | 9/1993 |
| GB | 794985 | 5/1958 |
| JP | 363058134 A | 3/1988 |

OTHER PUBLICATIONS

Patent Abstracts of Japan, Abstract of Japanese Patent "Method and Device of Detecting Casting Skin Surface Around Burr in Casting Burr Removing Work", Publication No. 63174857, Jul. 19, 1988, Japanese Application No. 62008545, Filed Jan. 16, 1987.

Patent Abstracts of Japan, Abstract of Japanese Patent "Method for Measuring Burr Shape and Dimensions Generated on Plate Shear", Publication No. 06066536, Mar. 8, 1994, Japanese Application No. 04245804, Filed Aug. 21, 1992.

Patent Abstracts of Japan, Abstract of Japanese Patent "Automatic Shape Tolerance Measuring Method and its Measuring Instrument", Publication No. 61111410, May 29, 1986, Japanese Application No. 59232367, Filed Nov. 6, 1984.

Extract from Delphion database relating to JP 2051001, "Method and Device for Measuring Height of Burr", Issued Feb. 21, 1990, Japanese Application No. 1988000200034, Filed Aug. 12, 1988.

Extract from Delphion database relating to JP 11153414, "Measuring Method of Burr Height and Mold Deviation of Molding", Issued Jun. 8, 1999, Japanese Application No. 1997000362423, Filed Nov. 21, 1997.

* cited by examiner

SENSOR DEVICE FOR BURR EXAMINATION

The invention relates to a sensor device for burr examination.

Burrs may result all over at places where workpieces are machined by means of metal cutting. For example, burrs may result on bores. Burrs can be an interference for various reasons. For example, no burrs should be present at separating surfaces which are to be sealed since, otherwise, the result of sealing will be influenced. It may be desirable for no projection of material to be present in the case of certain workpieces. Burrs which are present and drop off during assembly of components may be a nuisance. If they fall off during the operation of a unit, this may be destroyed. Burrs at the edges of the material of a workpiece to be coated may cause irregular lacquer densities. Sharp-edged burrs on outer workpiece surfaces may lead to injuries due to cuts.

It is, therefore, often necessary to carry out a burr examination after the machining of the workpiece, wherein this may have two aspects, namely a qualitative burr examination as to whether burrs are present and a quantitative examination as to whether a certain height tolerance of a burr has, for example, been exceeded.

Up to now, burr examinations have usually been carried out manually in that, for example, a corresponding workpiece surface is felt with the finger, the finger nail, a tooth pick, a cleaning tube with cotton wool lining, the tip of a pencil or a marker mandrel. Visual methods are also used in that, for example, a burr is examined with the naked eye, under a microscope or by means of a magnifying glass, an otoscope or by means of an endoscope.

Such methods are very time-consuming and the quantitative information content at least is relatively slight.

JP 06066536 A discloses a method for measuring the shape and dimensions of burrs, wherein the burr has resulted due to shearing. A corresponding plate edge is scanned via scanning means with a laser beam and light receivers of the position detection type are provided. Complicated optical means are necessary with a corresponding device. Since a large, free visible area must be present, inner tool surfaces cannot be scanned with it. The results of measurement are also very susceptible to soiling in the visible field which can influence the beam path.

The object underlying the invention is therefore to provide a sensor device for burr examination which can be used universally and in a simple manner.

This object is accomplished in accordance with the invention in that the burr-examination sensor device for the examination of burrs on a workpiece comprises at least one distance sensor with a detector head, wherein the detector head can be positioned at a distance to the workpiece and detector head and workpiece are movable relative to one another and wherein the detector head can be coupled to the workpiece electromagnetically or can be acted upon by the workpiece with an electromagnetic signal and the coupling to the workpiece or an electromagnetic reaction signal of the workpiece to the impinging signal are dependent on a distance between detector head and workpiece so that this distance can be determined without any contact and a workpiece surface can be scanned by the detector head without any contact.

As a result of the inventive use of a distance sensor as a separate component, wherein this distance sensor interacts with the workpiece and the interaction depends on the distance between distance sensor and workpiece, a burr examination may be carried out in a simple manner. The distance sensor forms a sensor field which is coupled locally to the workpiece. As a result, inner workpiece surfaces may also be examined when the distance sensor is inserted accordingly. The examination does, however, take place without any contact and so a simple and, in particular, mechanical use is facilitated.

The influence of soiling is also reduced in accordance with the invention since this has an effect, at the most, on the local sensor field.

Since the coupling of the distance sensor to the workpiece is influenced by the distance and the presence of a burr, on the other hand, alters the distance itself, quantitative information with respect to the burr may also be determined, for example, its extensions and as a result the type of burr.

The detector head advantageously has an active surface, via which a local coupling to the workpiece takes place or via which impinging signals are transmitted locally to a workpiece surface area and reaction signals received from this area. As a result, a corresponding workpiece surface—interior or exterior—may be scanned and the position of the active surface relative to the workpiece surface determines the scanning area which is examined for burrs. A local scanning may, therefore, be carried out in that detector head and workpiece are moved relative to one another, wherein the detection of burrs itself takes place without any contact and quantitative assessments may also be made.

It is favorable when detector head and workpiece are movable relative to one another parallel to a distance direction. As a result, the detector head may, for example, dip into a bore in the workpiece in order to examine this for burrs.

When a detector head is intended to be guided over a workpiece surface, a defined distance may also be set, as a result, in relation to this surface. Furthermore, it is advantageous when detector head and workpiece are movable relative to one another transversely to a vertical distance direction in order to be able, for example, to scan an outer workpiece surface.

It is particularly advantageous when a positioning device is provided for the positioning and movement of the detector head relative to the workpiece. A defined movement of the detector head relative to the workpiece may then be achieved and, in particular, this may be scanned in a defined manner.

For this purpose, it is favorable when the detector head is movable by the positioning device along linearly independent coordinate directions in order to thus obtain a maximum movement clearance.

Furthermore, it is favorable when the detector head is rotatable relative to the workpiece. For example, the detector head may then be introduced into a bore as a probe and turned in the bore in order to examine an entire circumferential area of an inner workpiece surface.

In an inexpensive variation, a positioning device for a tool for the machining of the workpiece is used as positioning device for a distance sensor. The positioning device for a tool must allow this the exact possibilities for movement which are required for the defined machining of the workpiece. These possibilities for movement may then be used for examining the workpiece by means of a distance sensor in order to also be able to examine the workpiece, in particular, automatically with respect to burrs. A measuring head of the inventive sensor device for burr examination may be moved along the workpiece for burr examination as exchange unit instead of the tool, in particular, immediately following the tool machining without the workpiece needing to be clamped. The coordinate system for the relative movement in relation to the workpiece is therefore maintained and so, in addition to the saving on time, no loss of accuracy occurs. The tool positioning device which is present in any case is therefore used as an exact positioning device for a distance sensor and so this can be positioned as required relative to the workpiece and the information concerning the relative position in relation to the workpiece is continuously available.

The detector head is favorably designed as a probe or arranged in a probe so that inner surfaces of the workpiece can also be scanned. The probe can, for this purpose, be inserted, in particular, into a bore in the workpiece in order to be able to detect, for example, burrs on transverse intersections.

In this respect it is favorable when electronic components of the device and, in particular, of the distance sensor are integrated entirely or partially in the probe so that the freedom from interference is increased.

A visual range of the distance sensor is preferably adjusted for the defined examination of a workpiece with respect to burrs. As a result of adjusting the visual range, the configuration and spatial position of a sensor field of the distance sensor with its active surface is selectively used with respect to the workpiece and the local area of the workpiece surface, which is examined, is adjusted selectively.

It may be favorable when a visual range and, thus, also a viewing direction of the distance sensor can be adjusted electromagnetically. As a result, the viewing direction can be adjusted selectively and also altered. For example, a sensor field may be turned. The adjustment may be brought about by adjusting the positioning of the detector head relative to the workpiece, wherein this is triggered by an electromagnetic signal or alternatively and in addition by adjusting the configuration of the sensor field at the detector head.

In this respect, it may be provided in a variation of one embodiment for the distance sensor to be designed and/or screened in such a manner that the electromagnetic coupling between detector head and workpiece is restricted to a specific visual range which is desired, in particular, for examining the workpiece.

The specific visual range may comprise a viewing direction which is essentially transverse to a longitudinal direction of a distance sensor. A distance sensor may then be displaced, for example, along an axis of a bore, wherein the walls of the bore can be examined during the displacement.

It may also be provided for the specific visual range to comprise a viewing direction which is essentially parallel to a longitudinal direction of a distance sensor. As a result, an outer surface of a workpiece may, for example, be examined when the distance sensor is guided over the workpiece.

Mixed forms are also possible, with which a viewing direction is set which is at a specific angle, for example, in relation to a longitudinal direction of a distance sensor; the visual range is advantageously adjusted to the special use.

It may be provided for a preliminary signal processing to take place in a measuring head and an evaluation unit to be provided for the burr examination. The signal supplied by the measuring head then contains the distance information and the evaluation unit evaluates this information with respect to the burr examination. The evaluation unit may be integrated in the measuring head or be separate from it. For example, it may be a PC, part of a control device for a processing line or a microcontroller circuit, wherein the evaluation can be carried out by means of software and/or a discrete circuit. A corresponding evaluation algorithm comprises, for example, the comparison with reference curves in order to indicate, for example, whether the quality of the workpiece is within or outside a tolerance range. The evaluation algorithm could, in a series of workpieces, also comprise a time comparison, according to which the formation of burrs is monitored in its development in time in order to carry out, for example, an indirect monitoring of the tool quality.

In a variation of one embodiment, the detection head is provided with contacts so that it can be connected to a device arranged at a distance. The detection head can, for example, be supplied with a voltage, wherein a power supply or the like is arranged at a distance from the detection head. An evaluation unit can also be arranged at a distance from the detection head and, in particular, at such a distance that this is not located in the area of the workpiece machining.

Alternatively, it may also be provided for the detection head to be designed as a remote unit which can be coupled cordlessly to a device arranged at a distance. The corresponding detection signals of the detection head are then transmitted to the remote device, for example, via infrared radiation.

In one advantageous embodiment, the distance sensor is an inductive sensor, with which the detection head is coupled inductively to a metallic workpiece. Distances to workpieces may be measured accurately with such inductive sensors. These are, in particular, not susceptible to soiling such as with oil since the inductive coupling remains essentially unaffected when the soiling is not metallic.

It may be provided for the distance sensor to have a metallic outer surface area which can be acted upon with a voltage. It is then possible to monitor whether a distance sensor possibly butts against a workpiece in that the metallic outer surface area is acted upon with a voltage potential. If this comes into contact with the workpiece, a warning signal can be generated which is passed to a positioning device, for example, in order to generate a counterreaction and move the distance sensor away from the workpiece again. A warning signal can also be generated when the measurement signal falls below or exceeds a predetermined threshold.

It may also be provided for the distance sensor to be an optical distance sensor, with which the detector head acts upon the workpiece with an optical signal and registers a reflection signal. Local distances between the detector head and the workpiece can also be determined in this way.

In order to form a local sensor field between workpiece and detector head, the light signal is preferably coupled in and/or coupled out in a fiber optic manner in order to be able to achieve a defined local viewing field in this way. The detector head as measuring head may be configured very compactly by means of the use of glass fibers and, in particular, a light scanner may then dip into bores, for example, like a probe.

A distance sensor can also be an ortho-inductive distance sensor which can scan a workpiece locally, optically and inductively for burrs, in particular, alternatively or combined as selected.

A further possibility is for the distance sensor to be a capacitive distance sensor, with which the detector head is coupled capacitively to the workpiece. Information concerning the distance between distance sensor and workpiece may also be obtained via the capacitive, electromagnetic coupling. In a variation thereof, the distance sensor is a coupled, inductive-capacitive distance sensor, with which an element is provided which can be coupled to the workpiece not only inductively but also capacitively. As a result, a double distance measurement may, to a certain extent, be carried out, namely, on the one hand, capacitively and, on the other hand, inductively. The more optimum method may be evaluated or a comparison can also be carried out, depending on the use. A signal is then coupled out from the inductive-capacitive distance sensor, for example, via a coaxial cable.

In a variation of one embodiment of an inventive sensor device for burr examination, a plurality of distance sensors is provided. A plurality of distance sensors has, accordingly, a plurality of sensor fields and, consequently, a workpiece can be examined with this plurality. In this respect, it may be provided for sensor signals of different distance sensors to be linked to one another. For example, a difference signal of distance sensors is evaluated and/or a cumulative signal of distance sensors is evaluated. As a result, a defined examination with respect to burrs and of burrs may be carried out and good, quantitative results may be obtained with respect to determining the type of burr and for burr extensions. As a result of the combination of several sensor signals by means of a suitable linking (e.g. sum or difference) the effects, in particular, of interference factors, such as temperature drift, material inhomogeneities and the like, can be reduced or the effect of measurement can be increased due to a combination of a measurement and a reference signal.

It may be provided for distance sensors of the sensor device for burr examination to have the same viewing direction in order to, for example, examine the same workpiece surface with various resolutions. It may also be provided for distance sensors of the sensor device for burr examination to have different viewing directions in order to be able to examine different workpiece surfaces at the same time. Distance sensors can, in particular, have viewing directions in opposite directions.

In an advantageous variation of one embodiment, the distance sensors of the plurality of distance sensors are fixed in position relative to one another. During any displacement, all the distance sensors are then displaced with one another at the same time and so, as a result, a defined movement of the sensor device for burr examination is possible relative to a workpiece.

It is particularly advantageous when the relative position of distance sensors of the sensor device for burr examination can be adjusted. The optimum distance between distance sensors can then be adjusted, depending on the use, for example, transversely to a longitudinal direction of the distance sensors and parallel to this. The distance sensors may then be arranged so as to be offset relative to one another which can be advantageous in certain uses. For example, when distance sensors dip into a bore an adaptation to the bore diameter can be carried out via the position adjustment.

For certain uses it may also be favorable when distance sensors have the same viewing plane so that a large surface area, for example, a circumferential surface within a bore can be scanned simultaneously when the sensor device for burr examination is displaced relative to the workpiece.

It may also be provided for distance sensors to have offset viewing planes so that the same workpiece surface can be examined several times, for example, during one procedure within a bore, namely, in particular, with different resolutions.

In a variation of one embodiment, two distance sensors are provided for a sensor device for burr examination and, in a further variation, three distance sensors which can carry out an examination of a workpiece surface.

The sensor device for burr examination is favorably adapted to the workpiece to be examined with respect to configuration of screening and/or viewing direction and/or operating frequency and/or a free zone in order to obtain an optimum examination as a function of the workpiece to be examined.

It is advantageous, in particular, for examining a large series of workpieces when a distance sensor is moved over a workpiece in a controlled and/or regulated manner in order to scan it. For this purpose, it is favorable when a distance to the workpiece determined by the distance sensor is a controlled variable. This is continuously detected and adjusted during the scanning via a positioning device such that it remains essentially constant. The absolute position of the detector head of the distance sensor in relation to the workpiece is known due to the positioning device and information concerning the formation of burrs on the workpiece may be obtained from the comparison of an actual output signal of the distance sensor with a reference curve, wherein the deviations from the reference curve also include quantitative information.

The object specified at the outset is accomplished, in addition, in accordance with the invention by the use of a distance sensor, which operates without any contact and can be positioned locally on a workpiece and can interact locally with it, wherein a distance between workpiece and distance sensor can be determined from the interaction, as burr examination sensor.

This use has the advantages already used in conjunction with the inventive device.

Additional, advantageous developments have already been explained in conjunction with the inventive device.

It is advantageous, in particular, when a local sensor field can be formed between the distance sensor and the workpiece, via which a distance between distance sensor and workpiece can be determined. As a result of the fact that the sensor field is formed locally, the distance sensor may be moved locally over the workpiece and examine this accordingly.

The following description of preferred embodiments serves to explain the invention in greater detail in conjunction with the drawings. These show:

FIGS. 1(*a*), (*b*), (*c*) various forms of burrs on a bore in a workpiece;

FIG. 8 a workpiece with a row of bores 1 to 9 with different diameters and different burr formations in a longitudinal sectional view from the side (FIG. 8(*a*)) and in a plan view (FIG. 8(*b*));

Figure 1A:
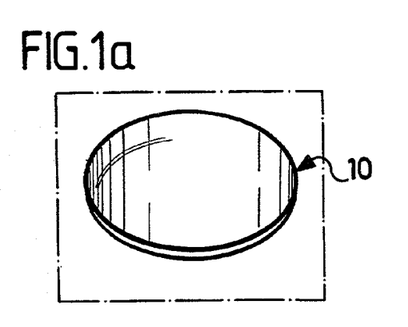

When a workpiece and, in particular, a metallic workpiece is machined by means of a metal-cutting tool, burrs can result on outer and inner surfaces, such as bore intersections of the workpiece. This is shown schematically in FIGS. 1(a) to (c) for bores.

Various types of burr are thereby differentiated; The so-called burr of burr type 1 which is designated in FIG. 1(a) as a whole as 10 is formed as a simple burr in the shape of a circumferential edge elevation, wherein the height of the burr is greater than 0.15 mm. A burr of the burr type 2 is likewise a simple burr which has a burr height of approximately 1.1 mm.

Figure 1B:
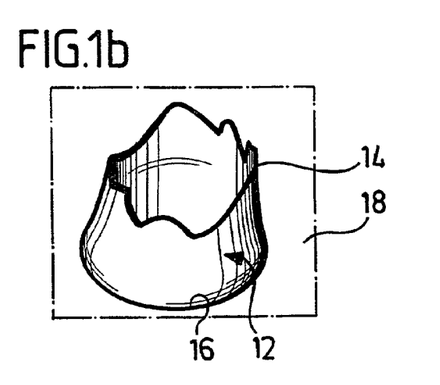

A burr of the burr type 3 which is designated in FIG. 1(b) as a whole as 12 is also called a crown burr since a circumferential edge 14 of this burr is of a prong-like design. The height of the burr of the burr type 3 is approximately 0.65 times the diameter of the bore 16 in the workpiece 18, on which the burr is formed.

A burr of the burr type 4 is a simple burr which comprises a bore cap which is suspended from the workpiece (not shown in the drawings).

Figure 1C:
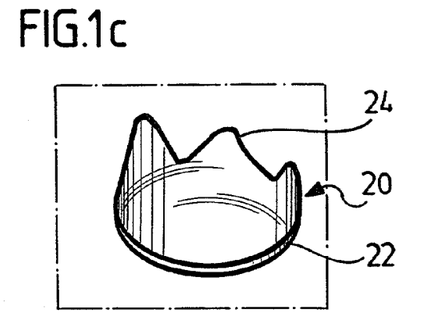

In the case of a burr of the burr type 5, which is designated in FIG. 1(c) as a whole as 20, the circumferential edge 22 is very irregular with respect to its height and prongs 24 are formed which are not, however, distributed around the entire edge 22 of the burr 20—in contrast to the burr of the burr type 3.

In accordance with the invention, a sensor device for burr examination is provided, with which it may, on the one hand, be detected whether a burr is in fact formed on a workpiece surface; quantitative assessments concerning a burr can also be obtained, in particular, by means of the inventive device, for example, what extensions it has or to what type of burr it belongs. By measuring a workpiece accordingly by means of the inventive sensor device for burr examination, different, important pieces of information may be obtained for the further processing of the workpiece, such as, for example, whether any subsequent machining is necessary with respect to removing a burr or reducing the size of a burr. On the basis of a series of workpieces, a tool examination may also be carried out to the extent that the burr alteration within the series of workpieces is monitored over time: For example, the blunting of a drilling tool may be determined from the type of burr formation on the edges of bores.

Figure 2:
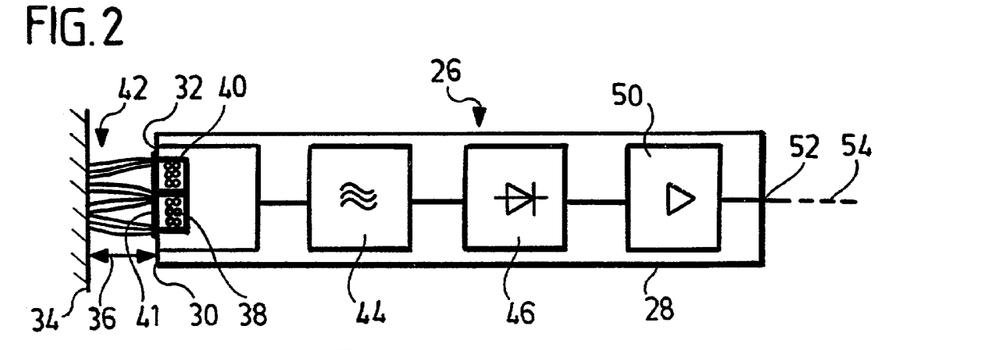
FIG. 2 a schematic illustration of a distance sensor which is used in an inventive sensor device for burr examination.

FIG. 2 shows schematically a first embodiment of an inventive sensor device for burr examination which is designated as a whole in the drawing as 26. This comprises a distance sensor 28 with a detector head 30. The detector head 30 has an active surface 32, via which this can be coupled electromagnetically to a workpiece 34, wherein the coupling is determined by a distance 36 between the active surface 32 of the detector head 30 and the workpiece 34.

In the embodiment shown in FIG. 2, the distance sensor 28 is an inductive proximity sensor which is coupled inductively to the workpiece 34, which must be produced for this purpose from a metallic material, via the generation of eddy currents. The detector head 30 of the distance sensor 28 has, for this purpose, a coil 38 facing the active surface 32 as inductive element, to which the metallic workpiece 34 is coupled inductively.

In the embodiment shown, the coil 38 is provided with a pot core 40. A base surface of the pot core 40 essentially defines the active surface 32; when approached, the surface corresponds to a pot core cap 41 of the active surface 32. A sensor field 42 of the distance sensor 28 is located in front of the active surface 32.

The distance sensor 28 also comprises, for example, an oscillator 44, a demodulator 46 and an output driver 50. An analogue output signal is made available at an outlet 52 of the distance sensor 28, for example, a voltage signal which is dependent on the distance between the active surface 32 of the detector head 30 and the workpiece 34.

Alternatively, it may be provided for a coil 38 of the distance sensor 28 to be without a core, wherein a metallic workpiece 34, for example, influences the amplitude of the oscillating oscillator 44 by way of inductive coupling and the amplitude and/or frequency and/or phase of the oscillator 44 is a measurement for the distance 36.

The interaction of the distance sensor 28 takes place only via the active surface 32 which defines the sensor field 42 in its configuration and positioning relative to the workpiece. The distance sensor 28 with its detector head 30 can be positioned locally on the workpiece 34 and interaction then takes place locally between the detector head 30 and the workpiece 34 by means of a local sensor field. If a burr is located in the sensor field 42, the electromagnetic (inductive) coupling between the active surface 32 and the workpiece 34 is influenced as a result and the output signal 52 is altered accordingly. As a result, local information is obtained concerning the workpiece, namely whether a burr is present, when the signal is altered accordingly and quantitative information can, on the other hand, be obtained concerning the burr from the signal alteration itself.

The distance sensor 28 in FIG. 2 has been described by way of example as an inductive distance sensor which is coupled inductively to the workpiece. It may, however, also be provided for the distance sensor to be designed as a capacitive distance sensor which is coupled capacitively to the workpiece 34. In this case, as well, the coupling is an electromagnetic coupling, wherein this electrostatic coupling is again influenced by the distance 36. In this case, as well, a burr examination may be carried out on the workpiece 34 proceeding from an output signal of a corresponding, capacitive distance sensor.

In the embodiment shown in FIG. 2, the active surface 32 is formed symmetrically around a longitudinal axis 54 of the distance sensor 28. The sensor field 42 is likewise formed symmetrically around this longitudinal axis 54 insofar as no coupled workpiece 34 is present or in the case of a coupled workpiece 34 this is likewise symmetric in relation to the longitudinal axis 54 of a distance sensor 28 positioned at a distance, at least in the area of the effective sensor field 42.

An effective sensor area of the distance sensor 28 (the sensor field 42) therefore has a visual range with a viewing direction which is essentially parallel to the longitudinal direction 54 of the distance sensor 28.

Figure 3:
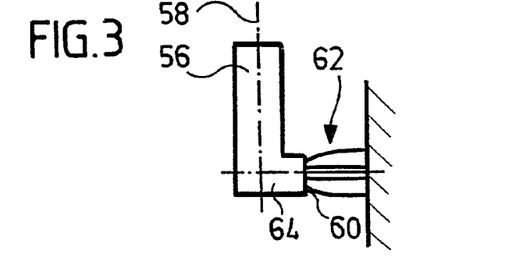
FIG. 3 a schematic illustration of an additional distance sensor which is used in a sensor device for burr examination.

It may also be provided, as shown schematically in FIG. 3 on the basis of a distance sensor 56 with a longitudinal direction 58, for an active surface 60 to be oriented transversely to this longitudinal direction 58 such that a corresponding visual range defined by a sensor field 62 has a viewing direction 64 which is oriented essentially transversely and, in particular, at right angles to the longitudinal direction 58 of the distance sensor 56.

The visual range of a distance sensor may be adjusted in a defined manner and, in particular, be restricted by screening elements in order to, for example, achieve a high local resolution as a result. Screening elements arranged accordingly influence the formation of the sensor field between the distance sensor and the workpiece. In the case of an inductive distance sensor, these may, in particular, be screening elements which influence the induction of current eddies in the metallic workpiece 34 or, in the case of a capacitive distance sensor, these may be screening elements which influence the formation of the electric field between an active surface and the workpiece.

An analog output signal is present at the outlet 52 and this contains the distance information for the distance between detector head 30 and workpiece. A separate evaluation unit is preferably provided, to which this signal of a measuring head is transmitted cordlessly or by means of a line (not shown in the drawings). The evaluation unit then determines from the burr information indirectly contained in the signal, by means of an evaluation algorithm, direct information concerning the burr formation, namely, in particular, concerning location and extension. For example, a comparison with a reference signal, which corresponds to the burr-free workpiece at the same sensor position, is carried out for this purpose.

A distance sensor may also be an optical distance sensor, such as, for example, a light scanner. This is shown schematically in FIG. 4 on the basis of a distance sensor 66. This has a detector head 68 with an active surface 70. Light acts upon the workpiece via the active surface and, in addition, a reaction signal of the workpiece is likewise received via the active surface 70, i.e. the light reflected back is received. A sensor field 72 is formed in front of the active surface, by means of which the workpiece can be scanned locally and with the aid of which a distance between the detector head 68 and the workpiece can be determined. The sensor field 72 is therefore formed locally between the distance sensor 66 and the workpiece.

Figure 4:
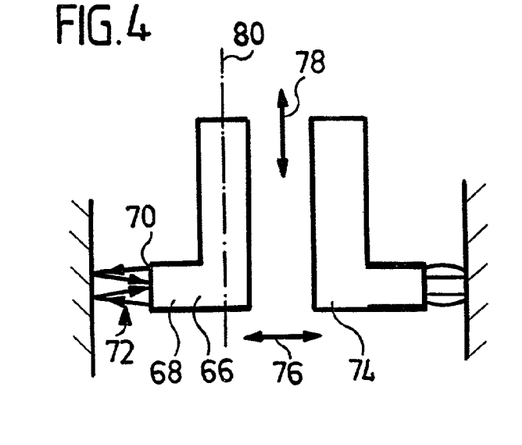
FIG. 4 a schematic illustration of one embodiment, with which a sensor device for burr examination comprises two distance sensors.

The detector head 68 with its active surface 70 itself represents the light source of the sensor field 72 and is likewise the receiver device for light reflected back from the workpiece; only the light acting on the active surface 70 is measured in order to obtain from this information concerning the distance of the detector head 68 from the workpiece.

In the case of an optical distance sensor 66, the sensor field 72 may be aligned very exactly and in a defined manner since the viewing direction of the sensor is determined by the light coupled out of the detector head 68 for acting on the workpiece. It may, in particular, be provided for light from the detector head 68 to be coupled out in a fiber optic manner. Light reflected back can also be coupled in again in a fiber optic manner in order to guide it to an optical evaluation unit.

Distances to non-metallic materials may also be measured optically by means of the measurement of light reflected back, and therefore the formation of burrs may be examined, for example, on ceramic materials or other plastic materials.

In FIG. 4, one embodiment of a sensor device for burr examination is shown schematically which comprises a plurality of distance sensors with respective detector heads. For example, an additional distance sensor 74 is provided next to the distance sensor 66. In the case of the distance sensor 74, this may be an optical, inductive or capacitive distance sensor. In principle, all possible combinations of distance sensors are possible within a sensor device for burr examination having a plurality of distance sensors. In a preferred embodiment, the distance sensors are, however, of the same type.

The distance sensors consisting of the plurality of distance sensors are preferably connected securely to one another so that during any displacement of the sensor device for burr examination comprising a plurality of distance sensors these are displaced together and their position relative to one another remains unchanged. However, it may also be provided for the relative position of the distance sensors in relation to one another to be adjustable, as indicated in FIG. 4 by the arrows 76 and 78. The distance sensors 66 and 74 may be pushed apart or pushed together like pincers, due to a determinable displaceability of these sensors along the direction 76, namely in a direction transverse to a longitudinal direction 80 of the respective distance sensors. As a result, a corresponding sensor device for burr examination may be adapted, for example, to a bore, into which such a sensor device is to be inserted for examining burrs on bore walls. As a result, the distance of the distance sensors 66, 74 in relation to the corresponding material surface to be examined (in the case of a bore of an inner material surface) may be adjusted in a defined manner and, as a result, the corresponding sensor fields of the distance sensors 66 and 74 may be adjusted in a defined manner.

In addition, a determinable adjustability of the distance sensors 66, 74 along the arrow 78, i.e. essentially parallel to the longitudinal direction 80 of the distance sensors 66, 74, may be adjusted. As a result, the associated sensor fields may be offset relative to one another with viewing planes, for example, transversely to the longitudinal direction 80 so that different height areas, for example, in a bore may be scanned at the same time by a sensor device for burr examination comprising a plurality of distance sensors.

If the sensor fields of the distance sensors 66, 74 are not offset relative to one another with respect to their height, a greater part of a circumferential surface in a bore may be scanned simultaneously when such a sensor device dips, for example, into the bore. If additional distance sensors are arranged so as to be distributed around the circumference, this area which can be scanned simultaneously is then increased.

It may also be provided for a sensor device comprising one distance sensor or a plurality of distance sensors to be turned within, for example, a bore preferably about an axis of symmetry of the bore in order to scan the circumferential walls of the bore completely in this way and therefore carry out an inventive burr examination.

It may also be provided for a difference signal and/or a cumulative signal to be formed in the case of a plurality of distance sensors, namely, in particular, when the distance sensors have the same viewing direction.

Figure 5:
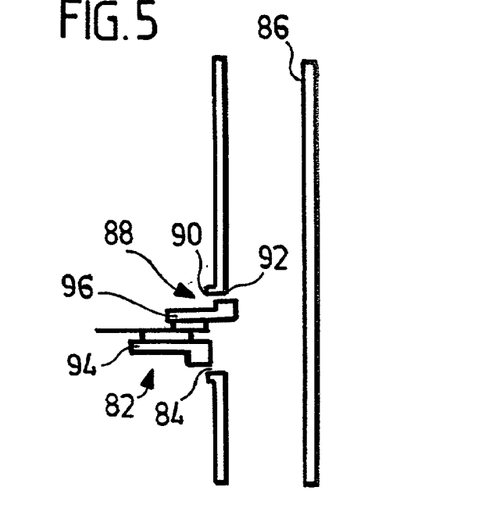
FIG. 5 a variation of an inventive sensor device for burr examination with likewise two distance sensors.

In FIG. 5, one embodiment of a sensor device 82 for burr examination is shown which serves to examine a bore 84 which opens into a further bore 86 so that an intersection 88 is present. Such an intersection 88 has an outer edge 90, on which burrs can be present, and an inner edge 92, on which burrs can likewise be present.

In the case of the sensor device 82, two distance sensors 94, 96 are arranged offset to one another at such a distance that the outer edge 90 and the inner edge 92 can be examined for burrs at the same time in one measurement procedure. The distance between the distance sensors 94, 96 corresponds essentially to a distance between outer edge 90 and inner edge 92. The formation of burrs on the inner edge 92 can, for example, be measured with the sensor 96 while the distance sensor 94 supplies information at the same time concerning the formation of burrs on the outer edge 90.

In FIGS. 4 and 5, sensor devices with a plurality of distance sensors are shown, with which the respective sensor fields have viewing directions in opposite directions so that workpiece surfaces located opposite one another can be examined. It may also be provided for a plurality of radial viewing directions to be set, for example, in the case of a corresponding number of distance sensors greater than two.

Figure 6:
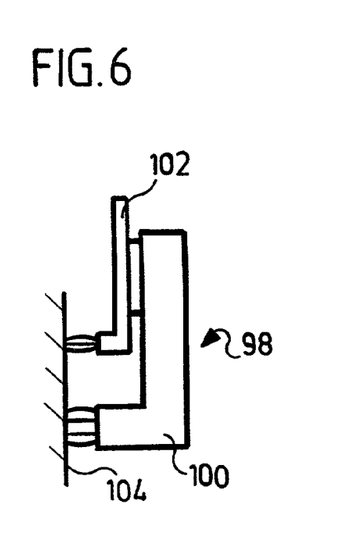
FIG. 6 a further variation with two distance sensors arranged so as to be axially spaced.

In FIG. 6, one embodiment of a sensor device 98 for burr examination is shown, with which a first distance sensor 100 and a second distance sensor 102 are provided which are offset relative to one another with respect to their height but have the same viewing directions. When a workpiece surface 104 is scanned due to displacement of the sensor device 98, the same surface area may therefore be scanned first of all by the one distance sensor and then by the other distance sensor. It may then be provided, in particular, for the two distance sensors 100, 102 to be of a different design, for example, to the extent that the first distance sensor 100 has a lower resolution and carries out a rough scanning, for example, in order to detect whether a burr is in fact present and the second distance sensor 102 has a finer resolution and a burr, the presence of which has been detected by the first distance sensor 100, can then be measured quantitatively by it.

A quicker scanning of workpiece surfaces may be achieved by an arrangement of distance sensors fixed relative to one another but offset in height since the resulting sensor field, with which the sensor device 98 for burr examination acts on the workpiece, is increased in accordance with the number of distance sensors 100, 102.

Figure 7:
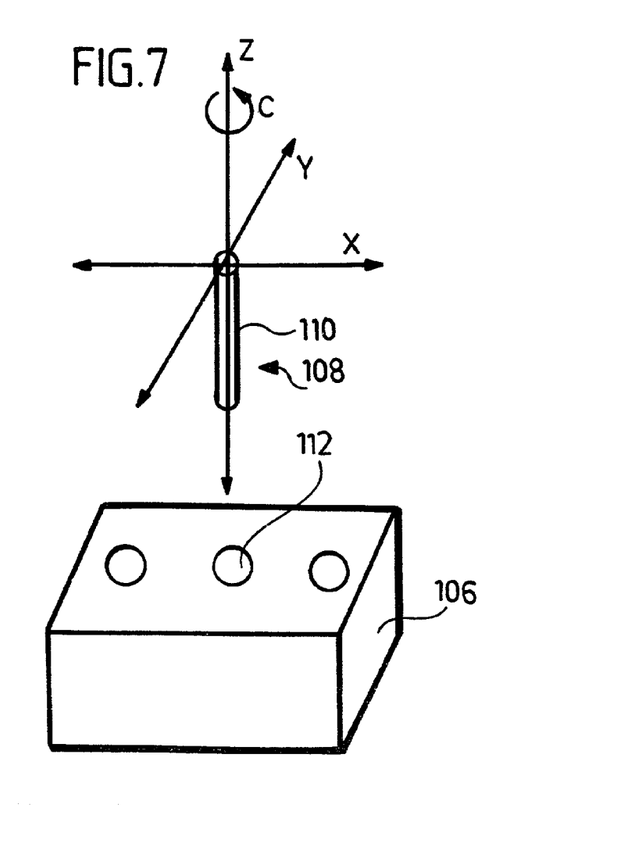
FIG. 7 schematically the possibilities for moving a distance sensor, which is held on a positioning device, relative to a workpiece.

For the selective scanning and examination of a workpiece 106 for burrs, a positioning device is, as indicated in FIG. 7, advantageously provided, by means of which a sensor device 108 for burr examination may be positioned relative to the workpiece 106 at it and at a certain distance to it. For example, the sensor device 108 is movable relative to the workpiece 106 with a distance sensor designed as a probe 110, namely in an X direction, Y direction and Z direction, wherein the movement in the Z direction determines the distance in height between the probe 110 and the workpiece 106. The probe 110 may dip, in particular, into bores 112 in the workpiece 106 in order to examine inner surfaces of the workpiece 106 for burrs which may have resulted, for example, due to intersections.

One possibility for moving the probe 110 is a positioning device with an X slide, Y slide and Z slide.

In addition, it may also be provided for the probe 110 to be rotatable, for example, about the Z axis (C movement according to FIG. 7) in order to be able to scan an inner circumferential surface of a bore 112.

During the machining of the workpiece 106 by means of a tool, a positioning device for the tool with respect to the workpiece 106 itself must be provided or a positioning device for the workpiece 106 relative to the tool. Combinations are also possible, with which the tool is moved in part for the relative positioning (for example, in Z direction) and the workpiece is moved in part (for example, in X direction and Y direction). It may be provided for the positioning device for the relative positioning between tool and workpiece 106 to be used for the relative positioning of the probe 110 in relation to the workpiece 106; following the machining of the workpiece an examination of the results of work can take place without the workpiece 106 needing to be transported. For example, an adapter for the workpiece-tool positioning device may be provided so that the probe 110 can be positioned relative to the workpiece 106 via this positioning device and the workpiece can be scanned locally in that the probe 110 is moved along outer and/or inner surfaces of the workpiece 106.

FIGS. 8 to 11 illustrate measurements which have been carried out with a sensor device for burr examination comprising an inductive distance sensor on a metal block with bores of different diameters. The metal block is shown schematically in FIGS. 8(*a*) in a side view and 8(*b*) in a plan view and designated as a whole as 114. This has continuous bores 1, 2, 3 with a small diameter, 4, 5, 6 with a medium-sized diameter and 7, 8, 9 with a large diameter. Burrs are formed on the bores 2, 3, 5, 6 and 8, 9 on a surface 116 of the metal block 114, wherein the type of burr is burr type 2 in the case of the bores 3, 6 and 9 (cf. FIG. 1(*a*)) and the burr in the case of the bores 2, 5 and 8 is burr type 3 (cf. FIG. 1(*b*)).

Figure 8A:
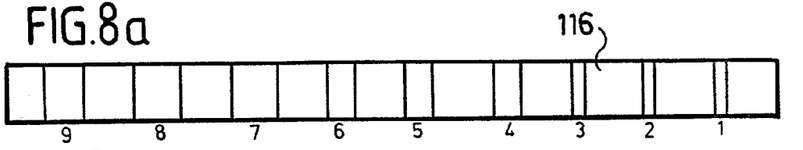
Figure 8B:
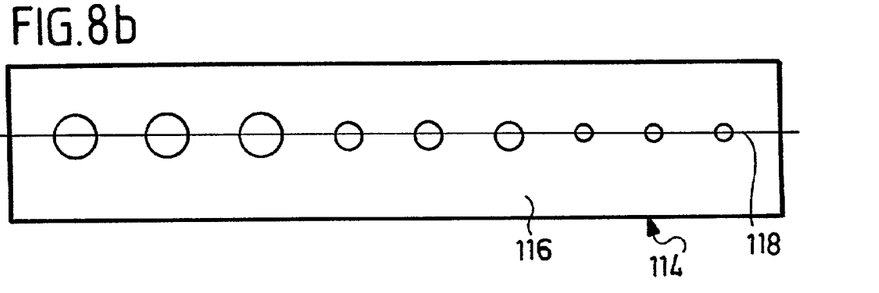

The inductive distance sensor 28 is moved along the line 118 with its longitudinal axis 54 aligned at right angles to the surface 116, wherein the line 118 is a line of symmetry of the diameters of the bores. The distance sensor 28 is positioned at a specific, fixed distance in relation to the surface 116, i.e. the distance of the active surface 32 of the associated detector head 30 is maintained during the displacement along the line 118. The sensor field 42 is directed towards the metal block 114.

Figure 9:
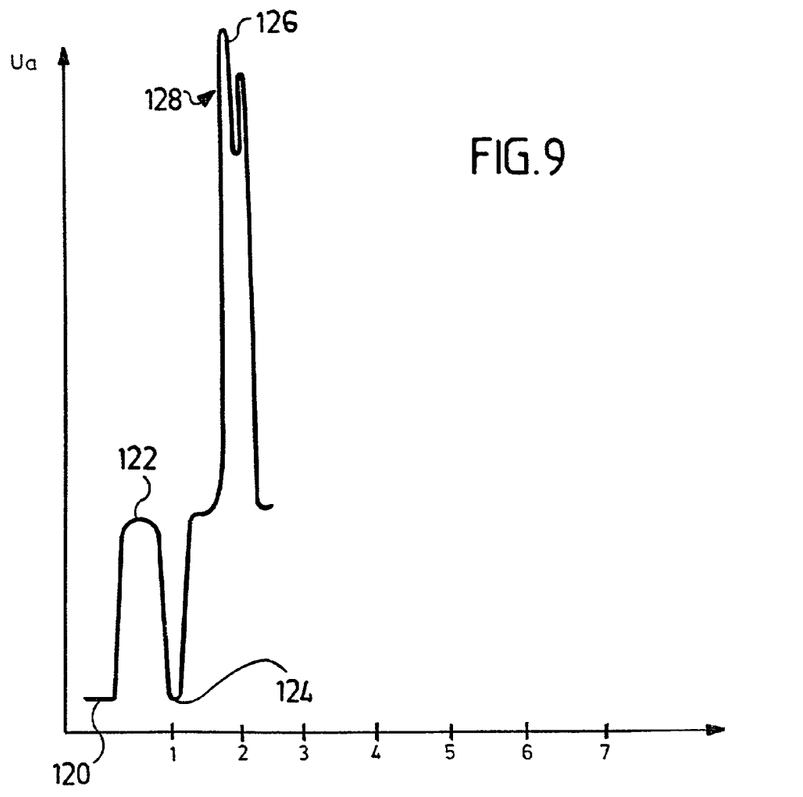
FIG. 9 a voltage curve supplied by a distance sensor when this is guided over the workpiece in its longitudinal direction symmetrically to the bore diameters at a certain distance (1.85 mm)

In FIG. 9, a first measurement graph is shown, wherein the distance sensor has been displaced over the surface 116 at a distance of 1.85 mm and a sensor with a small active surface has been used. The voltage $U_a$ is an output voltage of the sensor, wherein this becomes smaller in a positive ordinate direction, i.e. indicates an attenuation. A value in the vicinity of the abscissa of FIG. 9 therefore means that a large distance to the scanned surface section of the metal block 114 is present and a value far removed from the abscissa indicates that a correspondingly small distance has been detected.

At the reference numeral 120 in FIG. 9 the distance sensor 28 is positioned outside the metal block 114. If this is reached, the voltage is altered to a value 122 since energy is withdrawn from the sensor field due to current eddy induction in the metal block 114 and, as a result, the voltage is reduced. The distance sensor 28 can, to a certain extent, see into the burr-free bore 1, as indicated by the reference numeral 124. The bore 2 has a burr of the burr type 3. If this is reached, the voltage $U_a$ alters considerably, i.e. this drops considerably (reference numeral 126). The presence of a burr at the bore 2 may therefore be detected on the basis of the measurement graph of FIG. 9. Quantitative information concerning the detected burr may be ascertained from the minimum voltage reached and from the curve of the drop in voltage, namely, in particular, concerning its extensions and possibly also concerning its type. For example, the non-symmetric double peak 128 according to the measurement graph of FIG. 9 indicates that the burr at the bore 2 is a crown burr since no uniform burr height is present and also the considerable drop in voltage indicates a high burr height; the drop in voltage 126 therefore points to a burr of the burr type 3 which has actually been prepared on the metal block 114.

Figure 10:
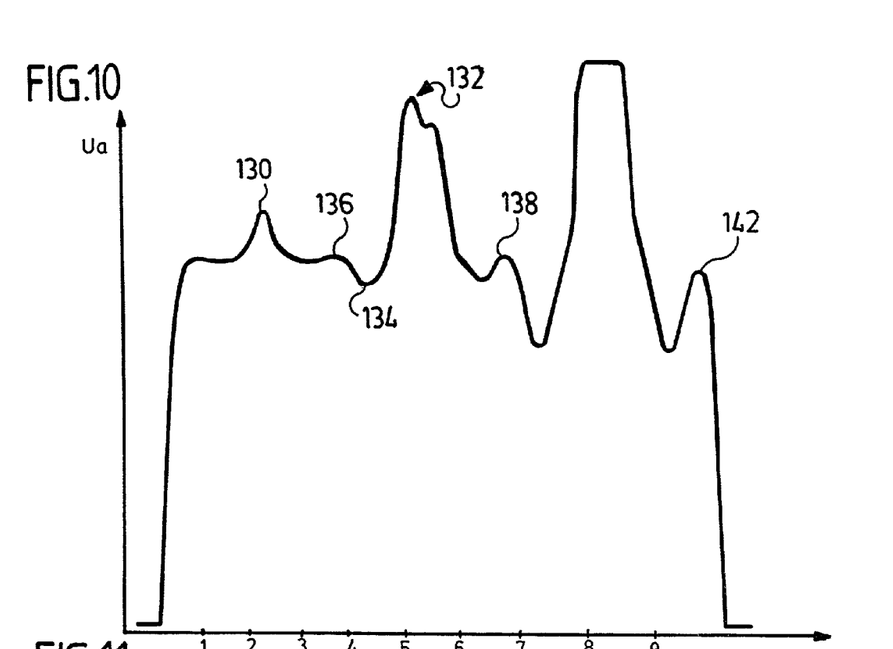
FIG. 10 the voltage curve of an additional distance sensor which has, in comparison with the sensor used for the measurement graph according to FIG. 9, a larger active surface and is guided over the workpiece at a different distance (5 mm)

In FIG. 10, a corresponding measurement graph is shown for the scanning of the metal block 114 with a distance sensor which has been guided over it along the line 118 at a distance of 4.6 mm. The diameter of the active surface is greater than in the case of the distance sensor which has been determined for determining the measurement graph of FIG. 9 and so the sensor field has a greater local extension. It is apparent that the distance sensor used for the measurement graph of FIG. 10 has a lower resolution. In particular, it looks less deeply into the bores. It detects the burr on the bore 2 (drop in voltage 130) but cannot resolve any double peak. However, a double peak 132 is resolved at the bore 5 which is an indication for the presence of a burr of the burr type 3 which has, in fact, been prepared at this point. The burr at the bore 3 is, however, detected only slightly. The distance sensor can look into the bore 4 to a certain extent, which is indicated by the reference numeral 134, but not into the bore 1. It can look even further into the bore 7 which has the greatest diameter. Whereas the burr of the burr type 2 at the bore 3 supplies only a weak signal 136, the burr at the bore 6 may be clearly identified (reference numeral 138).

The burr of the burr type 3 at the bore 8 is also identified, wherein the drop in voltage is, however, so considerable that a double peak can no longer be resolved. In this respect, it is to be noted that in the case of the burr of the burr type 3 the height of the burr depends on the diameter, i.e. the burr at the bore 8 has a relatively great height and so the distance sensor almost touches it.

Figure 11:
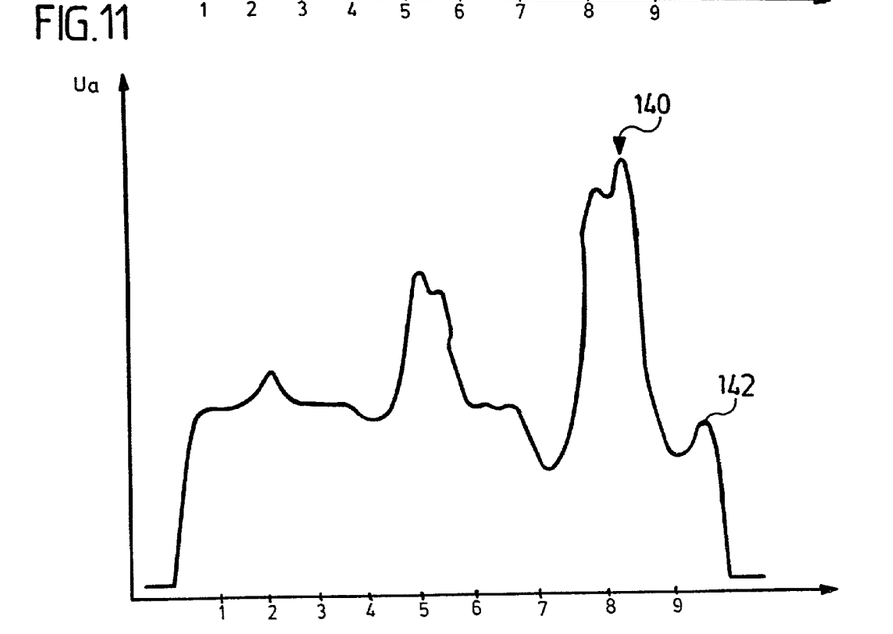
FIG. 11 a voltage curve of the distance sensor which has been used for the determination of the measurement graph according to FIG. 10 when this is guided over the workpiece at a greater distance (6.8 mm)
Figure 12A:
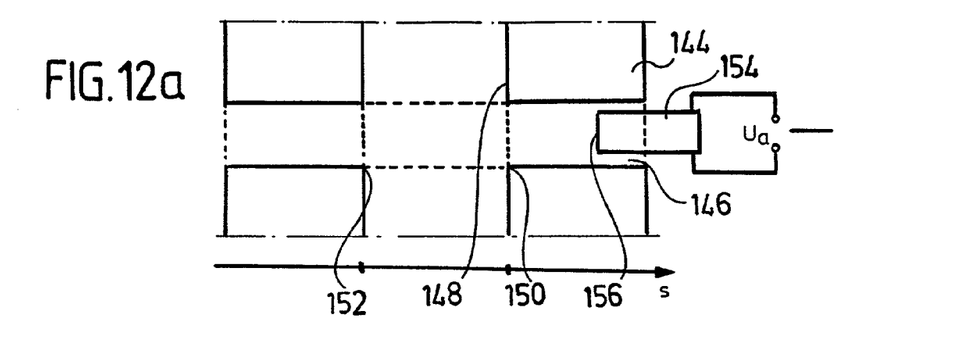
FIGS. 12(a)–(d) a workpiece with a bore intersection, wherein this bore intersection is free from burrs (FIG. 12(a)), has a burr with a low burr height at an edge of the intersection which faces an insertion opening for a distance sensor (FIG. 12(b)), has a burr with a greater height (FIG. 12(c)) and has a burr at an oppositely located intersection edge (FIG. 12 (d))
Figure 12B:
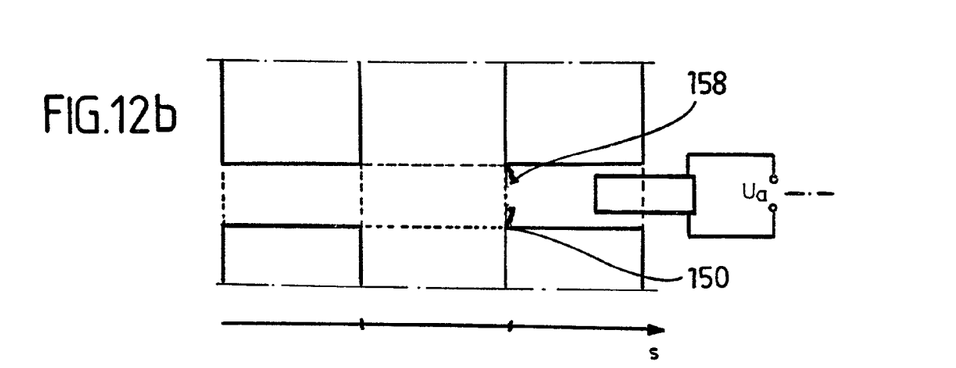
Figure 12C:
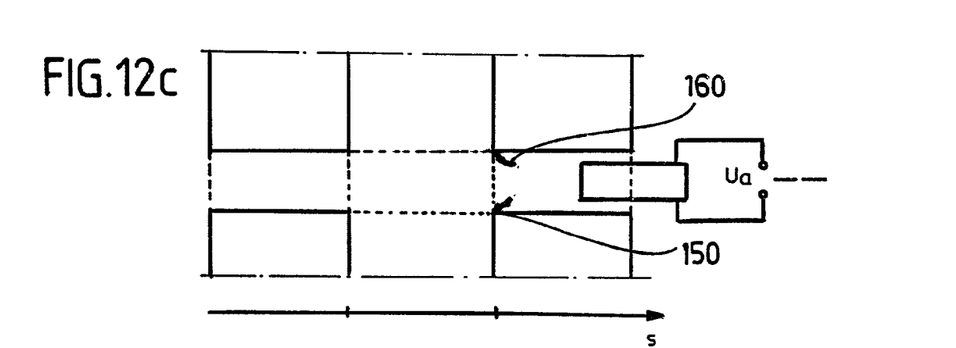
Figure 12D:
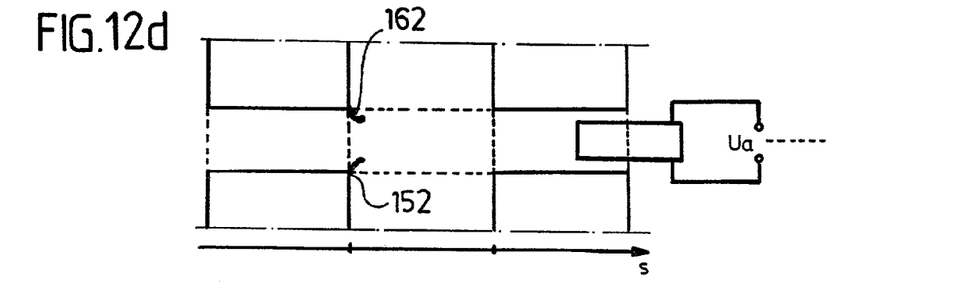

In the case of the measurement graph of FIG. 11, the same distance sensor has been used for the burr examination as in FIG. 10, wherein this has, however, been moved over the line 118 at a greater distance of 6.8 mm. A double peak 140 is now detected at the bore 8 which, as already mentioned above, indicates that the burr is a burr of the burr type 3. The burr of the burr type 2 at the bore 9 is also detected (reference numeral 142); this burr has also already been detected during the measurement which resulted in the measurement graph of FIG. 10.

The distance sensor 28 may also be moved over the metal block 114 in a controlled and/or regulated manner in order to carry out a burr examination on it. For this purpose, a distance determined via the distance sensor 28 as a controlled variable is, for example, kept essentially constant during the movement over the metal block 114 and the output voltage recorded. The absolute position of the detector head 30 in relation to the metal block 114 is known at any point of time and from a comparison of the output signal of the distance sensor 28 with a reference curve—which has been determined on a burr-free workpiece—, burrs may be detected with their position (relative deviation in relation to the reference curve) and their design (type and extent of the deviation).

As a result of an adapted use of correspondingly designed distance sensors, in particular, with respect to the size of the active surface and/or the viewing direction and/or an operating frequency of the distance sensor and/or the configuration of the sensor field, in particular, with respect to its directional dependence and/or distance dependence, a qualitative burr examination may be carried out for a specific use in accordance with the invention and also a quantitative burr examination.

For example, distance sensors with a large active surface may be used in order to scan burrs with a high burr height without any contact at a large distance. As a result, any abutment of a distance sensor on the workpiece with the burrs may be avoided to a great extent.

In this respect, it may also be provided for a sensor device for burr examination to have a distance sensor which has a metallic element which supplies a warning signal when the distance sensor butts against the workpiece in order to avoid damage to the distance sensor in this way. In this respect, it is to be noted that burrs can have very sharp edges and when the distance sensor comes into contact with a burr this could be impaired in its functionality or could even be destroyed.

Additional distance sensors may also be used, for example, with a smaller active surface in order to scan bores, in the case of which the resolution by means of a distance sensor with a large active surface was not sufficient in order to also be able to examine these bores for burrs in a defined manner.

Figure 13:
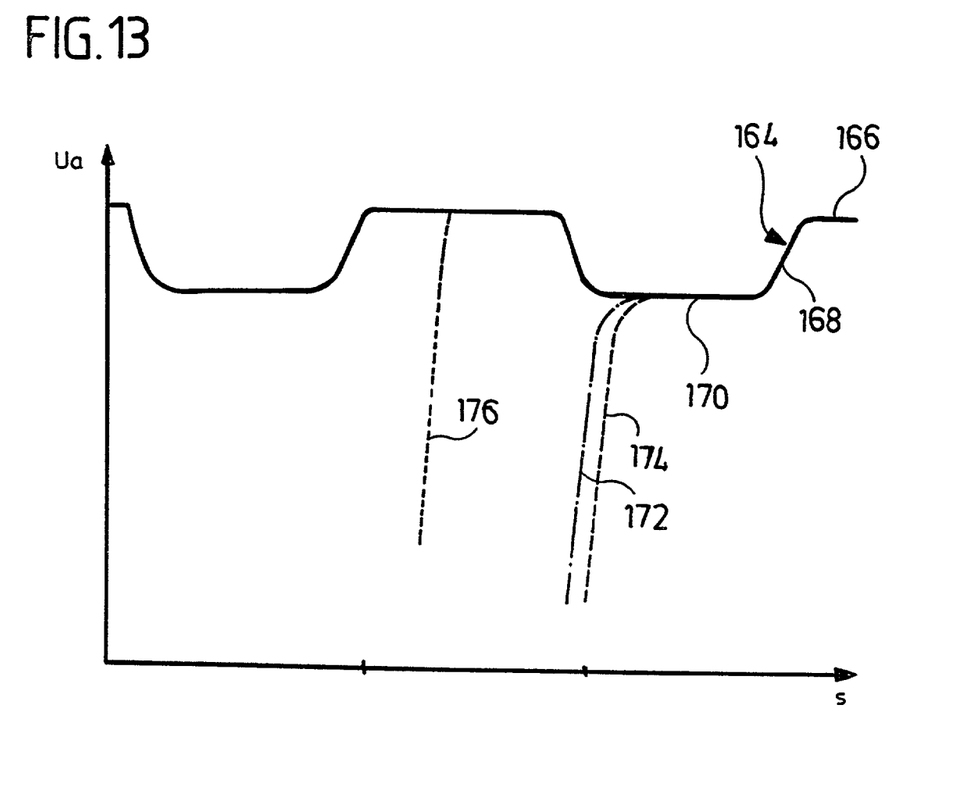
FIG. 13 the voltage curves which are supplied by a distance sensor which is displaced each time through a bore in the workpiece according to FIGS. 12(a) to (d).

In FIGS. 12 and 13, a measurement on a workpiece 114 is shown schematically which has a bore 146 and a transverse intersection 148, wherein burrs can be formed at a first edge 150 and a second edge 152.

An inductive distance sensor with a detector head 154 designed as a probe and an active surface 156 is introduced into the bore 146 and displaced in axial direction of this bore 146 in the direction of the second edge 152 and, in this respect, registers the output voltage U$a$ of the distance sensor as a function of the location s of the detector head 154.

In the case of the embodiment according to FIG. 12($a$), the edges 150 and 152 are free from burrs, in the case of FIG. 12($b$) a burr 158 is formed on the first edge 150, in the case of the workpiece according to FIG. 12($c$), a burr 160 is likewise formed on the edge 150 and has a burr height which is greater than that of the burr 158 according to FIG. 12($b$) and in the case of the workpiece according to FIG. 12($d$), a burr 162 is formed on the second edge 152.

The measurement graph according to FIG. 13 shows the voltage curve determined for the different workpieces according to FIGS. 12($a$) to ($d$). The voltage curve 164 results for the workpiece according to FIG. 12($a$) which is free from burrs. The voltage in FIG. 13 is applied along the path such that it increases with increasing distance from the abscissa. A high voltage 166 is therefore present outside the workpiece since no inductive coupling of the distance sensor takes place. If the distance sensor with its detector head 154 is then brought into the vicinity of the workpiece, the voltage drops due to the removal of energy via the inducted current eddies (reference numeral 168). Within the bore 146, insofar as the detector head 154 is aligned symmetrically to a bore axis, the voltage is uniform at a low level 170 and increases again when the transverse intersection 148 is reached. In the case of a large distance to the inner surfaces of the workpiece, the original voltage level 166 is reached in the transverse intersection 148 for the detector head 154 until the active surface 156 again exits from the transverse intersection 148 and enters the corresponding continuation of the bore 146.

If a burr 158 is formed on the edge 150, the voltage curve 172 results. The detector head registers in the vicinity of the first edge 150 that a change in the inductive coupling to the workpiece takes place and the voltage decreases considerably since the burr 158 is present. The position of the drop in voltage specifies where the burr is seated, i.e. what extension it has in relation to the direction of displacement. The steepness of the drop in voltage again supplies information as to what extent the burr is formed transversely to the direction of displacement. Quantitative information relating to the burr 158 can thus be obtained by adjusting the sensor field accordingly.

This is shown by way of example on the basis of the voltage curve 174 for the workpiece according to FIG. 12($c$) with the burr 160. This burr 160 has a greater height than the burr 158 according to FIG. 12($b$) but essentially the same transverse dimensions. The drop in voltage therefore occurs earlier since the burr 160 is reached earlier by the detector head 154 with its sensor field than the burr 158 in FIG. 12(*b*). The steepness of the voltage curves 172 and 174 is, however, very similar since the transverse dimensions of the burrs 158 and 160 are comparable.

The voltage curve 176 is finally obtained for the workpiece according to FIG. 12(*d*), with which a burr is formed on the second edge 152. A drop in voltage then follows proceeding from a higher voltage level since the detector head 154 is located in a transverse intersection area 148 and is thus coupled inductively to the workpiece to a lesser degree when it interacts for the first time with the burr 162. However, the location of the burr may again be determined by the position of the drop in voltage and its extension determined.

In accordance with the invention, a burr examination is carried out in that a distance sensor is positioned at a distance to the workpiece, wherein the distance sensor has a detector head with an active surface and a local sensor field is formed between the active surface and the workpiece. The distance of the detector head from the workpiece may be determined via this sensor field. The detector head is then moved over the workpiece or the workpiece is moved relative to the detector head and when burrs are present a corresponding distance signal generated by the distance sensor, from which, on the one hand, a qualitative reading is taken as to whether a burr is present and from which quantitative assessments concerning the type and the formation of the burr may be generated, is altered.

By configuring the size and alignment of the sensor field accordingly, the inventive sensor device for burr examination may be adapted to corresponding outer and inner workpiece surfaces to be examined and an adaptation may be achieved due to the corresponding evaluation in the distance sensor, for example, by selecting a specific oscillator frequency and the like.

The distance sensor is coupled, in particular, electromagnetically to a workpiece, for example, inductively or capacitively or is acted upon by the detector head with an electromagnetic signal and the reaction signal is received. In the case of an electromagnetic signal impingement, as well, the distance sensor is one having a local sensor field which is determined by an active surface of the detector head. In accordance with the invention, workpiece surfaces are scanned locally in order to carry out a burr examination—qualitatively and/or quantitatively.

The inventive sensor device for burr examination may also be used for examining edges, for example, for examining beveling and the like.

What is claimed is:

1. Burr-examination sensor device for the examination of burrs on a workpiece, comprising:
   at least one distance sensor with a detector head positionable proximate to the workpiece;
   said detector head and workpiece being movable relative to one another;
   said detector head having an active surface that is electromagnetically couplable to the workpiece via at least one of inductance and capacitance, for determining a distance between the detector head and the workpiece by scanning a workpiece surface with the active surface of the detector head in order to detect variations in at least one of inductance and capacitance indicative of burrs without any contact between said surfaces.

2. Sensor device for burr examination as defined in claim 1, wherein detector head and workpiece are movable relative to one another parallel to a distance direction.

3. Sensor device for burr examination as defined in claim 1, wherein detector head and workpiece are movable relative to one another transversely to a vertical distance direction.

4. Sensor device for burr examination as defined in claim 1, comprising a positioning device for the positioning and movement of the detector head relative to the workpiece.

5. Sensor device for burr examination as defined in claim 4, wherein the detector head is positionable by the positioning device along linearly independent coordinate directions.

6. Sensor device for burr examination as defined in claim 4, wherein the detector head is rotatable relative to the workpiece.

7. Sensor device for burr examination as defined in claim 4, wherein a positioning device for a tool for the machining of the workpiece is used as a positioning device for a distance sensor.

8. Sensor device for burr examination as defined in claim 1, wherein the detector head is designed as a probe or arranged in a probe.

9. Sensor device for burr examination as defined in claim 8, wherein the probe is insertable into a bore in the workpiece in order to detect burrs in the bore.

10. Sensor device for burr examination as defined in claim 8, wherein electronic components of the device are arranged entirely or partially in the probe.

11. Sensor device for burr examination as defined in claim 1, wherein a visual range of the distance sensor is adjusted.

12. Sensor device for burr examination as defined in claim 11, wherein a visual range of the distance sensor is adjustable electromagnetically.

13. Sensor device for burr examination as defined in claim 11, wherein the distance sensor is designed and/or screened in such a manner that the electromagnetic coupling between detector head and workpiece is restricted to a specific visual range.

14. Sensor device for burr examination as defined in claim 11, wherein the specific visual range comprises a viewing direction essentially transverse to a longitudinal direction of a distance sensor.

15. Sensor device for burr examination as defined in claim 11, wherein the specific visual range comprises a viewing direction essentially parallel to a longitudinal direction of a distance sensor.

16. Sensor device for burr examination as defined in claim 1, wherein a preliminary signal processing takes place in a measuring head and an evaluation unit for the burr examination is provided.

17. Sensor device for burr examination as defined in claim 16, wherein an evaluation algorithm compares a measurement signal with a reference curve.

18. Sensor device for burr examination as defined in claim 1, wherein the detector head is provided with contacts so that it is connectable to a device arranged at a distance.

19. Sensor device for burr examination as defined in claim 1, wherein the detector head is designed as a remote unit couplable cordlessly to a device arranged at a distance.

20. Sensor device for burr examination as defined in claim 1, wherein a distance sensor is an inductive sensor, the detector head being coupled inductively to a metallic workpiece with said sensor.

21. Sensor device for burr examination as defined in claim 20, wherein the distance sensor has a metallic outer surface area acted upon with a voltage.

22. Sensor device for burr examination as defined in claim 1, wherein a distance sensor is an ortho-inductive distance sensor, the detector head being coupled inductively to a metallic workpiece and the workpiece being acted upon by the detector head with an optical signal and a reflection signal being registerable by the detector head with said distance sensor.

23. Sensor device for burr examination as defined in claim 1, wherein a distance sensor is a capacitive distance sensor, the detector head being coupled capacitively to the workpiece with said distance sensor.

24. Sensor device for burr examination as defined in claim 1, wherein the distance sensor is a coupled inductive-capacitive distance sensor, an element couplable to the workpiece not only inductively but also capacitively being provided with said distance sensor.

25. Sensor device for burr examination as defined in claim 1, wherein a plurality of distance sensors is provided.

26. Sensor device for burr examination as defined in claim 25, wherein sensor signals of different distance sensors are linked to one another.

27. Sensor device for burr examination as defined in claim 25, wherein a difference signal of distance sensors is evaluated.

28. Sensor device for burr examination as defined in claim 25, wherein a cumulative signal of distance sensors is evaluated.

29. Sensor device for burr examination as defined in claim 25, wherein distance sensors of the sensor device for burr examination have the same viewing direction.

30. Sensor device for burr examination as defined in claim 25, wherein distance sensors of the sensor device for burr examination have different viewing directions.

31. Sensor device for burr examination as defined in claim 30, wherein distance sensors of the sensor device for burr examination have viewing directions in opposite directions.

32. Sensor device for burr examination as defined in claim 25, wherein the distance sensors are fixed in position relative to one another.

33. Sensor device for burr examination as defined in claim 25, wherein the relative position of the distance sensors of the sensor device for burr examination is adjustable.

34. Sensor device for burr examination as defined in claim 25, wherein distance sensors have the same viewing plane.

35. Sensor device for burr examination as defined in claim 25, wherein distance sensors have offset viewing planes.

36. Sensor device for burr examination as defined in claim 25, wherein two distance sensors are provided.

37. Sensor device for burr examination as defined in claim 25, wherein three distance sensors are provided.

38. Sensor device for burr examination as defined in claim 1, wherein the sensor device for burr examination is adapted to the workpiece to be examined with respect to configuration of screening and/or viewing direction and/or operating frequency and/or a free zone.

39. Sensor device for burr examination as defined in claim 1, wherein a distance sensor is moved over a workpiece in a controlled and/or regulated manner in order to scan it.

40. Sensor device for burr examination as defined in claim 39, wherein a distance to the workpiece determined by the distance sensor is a controlled variable.

41. Use of a distance sensor for examining burrs in a bore of a workpiece, said sensor operating using at least one of electrical inductance and capacitance without contacting the workpiece and being positionable adjacent the workpiece and able to interact with the workpiece in close proximity thereto, wherein a distance between the workpiece and the distance sensor indicative of the presence or absence of a burr is determinable from the interaction.

42. Use of a distance sensor as defined in claim 41, wherein the distance sensor is coupled to the workpiece capacitively.

43. Use of a distance sensor as defined in claim 41, wherein the distance sensor is coupled to the workpiece inductively.

44. Use of a distance sensor as defined in claim 41, wherein a local sensor field is adapted to be formed between the distance sensor and the workpiece, a distance between distance sensor and workpiece being determinable via said field.

* * * * *